United States Patent [19]

Patton

[11] 4,035,404

[45] July 12, 1977

[54] CYANOFORMAMIDYL ISOCYANATES AND SYNTHESIS THEREOF

[75] Inventor: Tad L. Patton, Baytown, Tex.

[73] Assignee: Exxon Research and Engineering Company, Linden, N.J.

[21] Appl. No.: 261,124

[22] Filed: June 8, 1972

Related U.S. Application Data

[60] Division of Ser. No. 76,590, Sept. 29, 1970, Pat. No. 3,684,773, which is a continuation-in-part of Ser. No. 685,281, Nov. 24, 1967, abandoned, and Ser. No. 685,311, Nov. 24, 1967, Pat. No. 3,591,562.

[51] Int. Cl.$^2$ .......... C07C 119/042; C07C 119/045; C07C 119/048
[52] U.S. Cl. ............... 260/453 AR; 260/77.5 CH; 260/77.5 R; 260/453 A; 260/453 AL
[58] Field of Search ... 260/453 A, 453 AR, 453 AL, 260/453 P

[56] References Cited
PUBLICATIONS

Petersen: Annalen der Chemie, vol. 562, p. 211, (1949).

*Primary Examiner*—Dolph H. Torrence
*Attorney, Agent, or Firm*—David A. Roth

[57] ABSTRACT

The monoadduct of a diisocyanate and hydrogen cyanide, a cyanoformamidyl isocyanate, is produced by he reaction of 1 mole of a diisocyanate with 1 mole of hydrogen cyanide. Heterocyclic polymers are produced by the head-to-tail polymerization of cyanoformamidyl isocyanates in an appropriate solvent and in the presence of an effective catalyst.

10 Claims, No Drawings

CYANOFORMAMIDYL ISOCYANATES AND SYNTHESIS THEREOF

CROSS-REFERENCE TO RELATED APPLICATIONS

This is a division of application Ser. No. 76,590, filed Sept. 29, 1970, now U.S. Pat. No. 3,684,773, which is a continuation-in-part of Ser. No. 685,281, filed Nov. 24, 1967, now abandoned, and Ser. No. 685,311, filed Nov. 24, 1967, now U.S. Pat. No. 3,591,562.

BACKGROUND OF THE INVENTION

1. Field of the Invention

The present invention is directed to new compositions of matter having the following formula:

$$OCN-R-\underset{H}{N}-\underset{\underset{O}{\parallel}}{C}-CN \quad (I)$$

where
R is the organic moiety of the diisocyanate from which the cyanoformamidyl isocyanate is produced and which is aliphatic, alicyclic, aromatic, or mixtures thereof and functionally substituted derivatives thereof.

The present invention is further directed to the heterocyclic polymers produced by the polymerization of cyanoformamidyl isocyanates. These polymers may be characterized by the following general repeating unit:

(II)

where:
$R_1$ and $R_2$ are the organic moiety from the cyanoformamidyl isocyanate and X is NH or N-acyl.

2. Prior Art

The reaction of monoisocyanates with hydrogen cyanide is known as disclosed by W. Dieckmann et al., *Berichte* 38, 2977 (1905). It has also been disclosed by S. Petersen in *Annalen der Chemie* 562, 205–226 (1949) that hexamethylene dicyanoformamide is formed by the reaction of hydrogen cyanide with hexamethylene diisocyanate. There is no disclosure, however, of the formation of cyanoformamidyl isocyanates by the reaction of diisocyanates with hydrogen cyanide.

An article in *Die Macromolekulare Chemie* 78, 186 (1964) by Oku et al. discloses:

"Starting from diisocyanates and hydrogen cyanide poly(5-imino hydantoins) have been prepared by the following two methods: (1) polyaddition between a diisocyanate and a di(carbamoyl cyanide), which corresponds to a 1:2 diisocyanate-hydrogen cyanide adduct. (2) hydrogen cyanide eliminating polymerization (polycondensation) of a di(carbamoyl cyanide). The former method generally gave more satisfactory results."

SUMMARY OF THE INVENTION

The present invention may be briefly described and summarized as involving the method of producing the cyanoformamidyl isocyanate as new compositions of matter as set forth in Formula I above. The cyanoformamidyl isocyanates are the mono-adducts formed by the reaction of one mole of diisocyanate with one mole of hydrogen cyanide in an appropriate solvent and with an effective catalyst.

The present invention is further directed to the heterocyclic polymers produced by the polymerization of cyanoformamidyl isocyanates which contain repeating units which include two imidazolidine rings. The heterocyclic polymers so produced as new compositions of matter are set forth in Formula II above.

DESCRIPTION OF THE PREFERRED EMBODIMENTS

The reaction of 2 moles of hydrogen cyanide with 1 mole of diisocyanate produces a dicyanoformamide. The formation of a cyanoformamidyl isocyanate (the mono adduct of the diisocyanate) involves the same reaction, but only one of the isocyanate groups participates in the reaction. The successful formation of a cyanoformamidyl isocyanate is dependent upon the structure of the diisocyanate, the solvent used for the reaction, the temperature of the reaction, and the compound used to catalyze the reaction. Diisocyanates in which the isocyanate groups do not have equivalent reactivity form cyanoformamidyl isocyanates much more easily than those in which the isocyanate groups have equivalent reactivity. The most favorable conditions for the formation of the cyanoformamidyl isocyanate are low temperature, the use of a solvent in which the product has low solubility while the starting diisocyanate has a high solubility, and the use of a catalyst which does not catalyze the further reaction of a cyanoformamidyl group with an additional isocyanate group under the reaction conditions.

The reaction to produce the cyanoformamidyl isocyanates of the present invention may be illustrated by the following equation:

$$OCN-R-NCO + HCN \xrightarrow[\text{Solvent}]{\text{cat}} OCN-R-\underset{H}{N}-\underset{\underset{O}{\parallel}}{C}-CN \quad (1)$$

The diisocyanates which may be used in the reaction with hydrogen cyanide are characterized by the formula:

$$OCN-R-NCO \quad (III)$$

where:
R is the organic moiety of the diisocyanate which may be aliphatic, alicyclic, aromatic, or mixtures thereof and functionally substituted derivatives thereof.

Thus, the diisocyanates may be selected from a broad group having a large variety of organic moieties. The organic moieties of the diisocyanates may be substituted with functional groups such as sulfoxy, sulfonyl, alkoxy, aryloxy, ester, alkylthio, arylthio, nitro, and the like, which do not react with the isocyanate group or with hydrogen cyanide. Functional groups which have active hydrogen atoms (i.e., carboxylic acids, phenols, amines, etc.) should not be present.

Each diisocyanate is characterized by a specific organic hydrocarbon moiety. For example, those diisocyanates having an aliphatic hydrocarbon moiety are exemplified by tetramethylene diisocyanate; hexamethylene diisocyanate; dodecamethylene diisocyanate;

2,2,4-trimethyl hexamethylene diisocyanate; and the like. Diisocyanates characterized by having aromatic hydrocarbon moieties are exemplified by m-phenylene diisocyanate; p-phenylene diisocyanate; biphenylene diisocyanate; 1,5-naphthalene diisocyanate and the like. A diisocyanate having an alicyclic hydrocarbon moiety is 1,4-diisocyanato cyclohexane and 3-isocyanatomethyl-3,5,5-trimethylcyclohexyl isocyanate. The diisocyanates containing more than one type of hydrocarbon moiety are exemplified by toluene diisocyanate, durene diisocyanate, 4,4'-diphenylmethane diisocyanate; 3,3'-dimethyl-4,4'-biphenylene diisocyanate; 4,4'-diphenylisopropylidene diisocyanate; p-xylene diisocyanate; m-xylene diisocyanate; 4,4'-methylene bis(cyclohexyl isocyanate); 4-(4-isocyanatocyclohexyl) phenylisocyanate; 4-isocyanatobenzyl isocyanate; and the like. It is noted by the foregoing examples that the isocyanate groups in each of the diisocyanates are attached to the same or different organic moieties. Further, diisocyanates which have the organic moiety functionally substituted may also be used and are exemplified by 4,4'-diphenylsulfone diisocyanate; 4,4'-diphenyl ether diisocyanate; 3,3'-dimethoxy-4,4'-biphenylene diisocyanate; di(3-isocyanatopropyl) ether; tetrafluoro-p-phenylene diisocyanate; tetrafluoro-m-phenylene diisocyanate; 4,4'-diisocyanate-octaflurobiphenyl; and the like. Further, specific diisocyanates which may be used in the present invention are found in patents, articles, or organic textbooks; a specific example being the paper "Mono and Polyisocyanates" by W. Sieflken, Annalen der Chemie 562, 6-136 (1949), which is incorporated herein by reference.

Under the reaction conditions for the above reaction (1), the choice of the catalyst is critical in that it must not catalyze the reaction of free isocyanate groups with cyanoformamidyl groups to form polymer. Catalysts which have been found effective are dibutyl tin diacetate; dibutyl tin bis(isooctylmaleate); 2-picoline; pyridine; lutidine; N,N-dimethylaniline, N,N-diethylaniline; quinoline, and the like.

Suitable solvents to be used in forming the cyanoformamidyl isocyanates are benzene, toluene, xylene, chlorobenzene, and mixtures thereof with petroleum ether, hexane, and other aliphatic solvents. A preferred solvent is one in which the cyanoformamidyl isocyanate is insoluble whereas the diisocyanate from which it is produced is soluble.

The reaction of the diisocyanate with hydrogen cyanide to form the cyanoformamidyl isocyanates of the present invention is normally carried out at −10° to +35° C., preferably at 0° to 20° C., and under anhydrous conditions.

POLYMERIZATION OF CYANOFORMAMIDYL ISOCYANATES

The formation of the heterocyclic rings in the polymers of the present invention produced by the polymerization of cyanoformamidyl isocyanates directly involves reactions (2) and (3) which are set forth as follows:

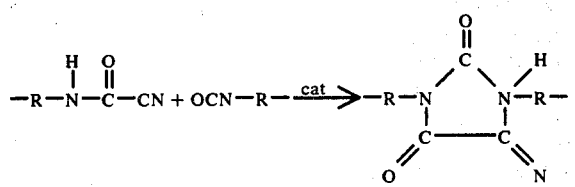

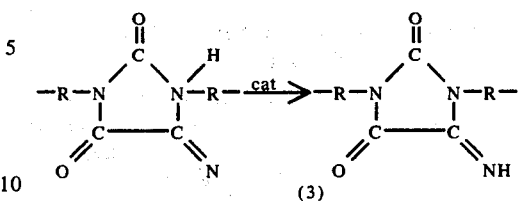

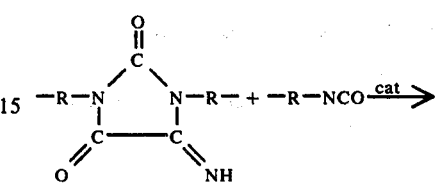

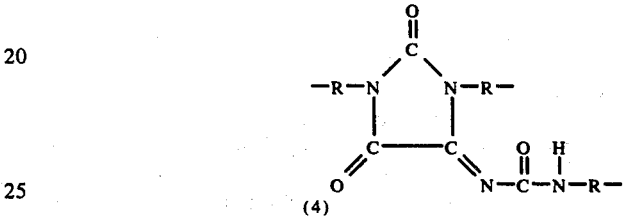

The reaction (4) is a side reaction which may occur and, if it occurs, results in branching and/or cross-linking. This reaction (4) can be limited by controlling the reaction temperature. As is illustrated in the reactions above, a catalyst is required. In polymerization of the cyanoformamidyl isocyanates, the choice of compounds which will catalyze the desired reactions are a wide variety of compounds. These compounds include the tertiary nitrogen compounds which have no active hydrogen atoms including the tertiary amines such as triethyl amine, triethylene diamine, 1-aza,-3,3,7,7,-tetramethyl bicyclo (3.3.0) octane, 1-methyl piperidine, N,N-dimethylaniline, N-methyl dicyclohexylamine, N-N-dimethylcyclohexyl amine, N-cyclohexylpiperidine, and N-cyclohexyl morpholine; heterocyclic bases such as pyridine, 2-picoline, 4-picoline, 3-picoline, 2,6-lutidine, 2,4-lutidine, and quinoline; phosphorous compounds such as triphenyl phosphine and tributyl phosphine; tin compounds such as dibutyl tin dilaurate, dibutyl tin diacetate, bis(tributyl tin) oxide, dibutyl tin bis(2-ethylhexoate), dibutyl tin bis(isoctylmaleate), and tetrabutyl tin; and lead compounds such as trimethyl plumbyl acetate and 1-(tri-n-butyl plumbyl) imidazole.

The polymerization of cyanoformamidyl isocyanates may be carried out in a suitable solvent such as the dipolar aprotic solvents, such as dimethylformamide, dimethylsulfoxide, hexamethylphosphoramide and the like which are preferred. The polymerization is carried out preferably under ambient and anhydrous conditions. The preferred temperatures are within the range of 10° to 35° C. At higher temperatures increased cross-linking occurs so that insoluble polymers may be produced.

The heterocyclic polymers produced by the polymerization of a cyanoformamidyl isocyanate contain repeating units which include two imidazolidine rings. The polymer may be characterized by the following general repeating unit:

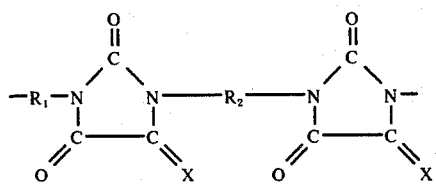

where:
R₁ and R₂ are the organic moiety from the cyanoformamidyl isocyanate and X is NH or N-acyl.

The polymers produced by the polymerization of a single cyanoformamidyl isocyanate will have repeating units where $R_1$ and $R_2$ are the same; however, $R_1$ and $R_2$ may be different if a mixture of cyanoformamidyl isocyanates are used. The polymers produced by the polymerization of cyanoformamidyl isocyanates are thus characterized by the imino and oxo groups on the imidazolidine rings being located in the same position (4 and 5 respectively) on each sequential imidazolidine ring. The particular structure of the polymers produced using a mixture of cyanoformamidyl isocyanates is dependent upon the reactivity of the respective cyanoformamidyl isocyanates and thus block or random copolymers may be produced.

The cyanoformamidyl isocyanates of the present invention and their preparation together with the polymerization of cyanoformamidyl isocyanates to form the polymers of the present invention are illustrated by the following examples, which are set forth for illustration and are not to be considered to be limiting the present invention.

EXAMPLE 1

A solution of 9.2 grams (0.34 moles) of hydrogen cyanide in 100 ml. of toluene was added to 52.2 grams (0.3 moles) of toluene 2,4-diisocyanate at 5° C. After the addition of 4ml. of dibutyl tin diacetate, the solution remained at 5°–10° C. for 4 hours. The reaction solution then slowly warmed to room temperature, and after an hour a white solid began to form. After remaining at room temperature overnight, 9.5 grams of a white solid was collected. The infrared spectrum of the product exhibited absorption maxima at 3.08, 4.40, and 6.0 microns.

Analysis Calculated for: $C_{10}H_7N_3O_2$ : C, 59.71; H, 3.51; N, 20.88. Found : C, 59.48; H, 3.58; N, 20.74.

These analyses and infrared spectrum are consistent with the structure of methyl-1,3-phenylene cyanoformamidyl isocyanate. The product melted at 128°–130° C. with subsequent resolidification which apparently was due to polymerization.

EXAMPLE 2

A solution of 126 grams (0.75 moles) of hexamethylene diisocyanate, 10 grams of pyridine, and 100 grams of toluene was added to a solution of 20.5 grams (0.76 moles) of hydrogen cyanide in 159 grams of toluene at 5° C. in a nitrogen atmosphere. The solution was stirred and allowed to slowly warm to room temperature overnight. The white product which precipitated was filtered and washed with petroleum ether to remove unreacted diisocyanate which may adhere to the product. The dry solid weighed 30 grams and melted at 92°–127° C. The infrared spectrum of the product exhibited absorption maxima of 3.09 (<N—H), 4.45 (strong characteristic of isocyanate group), and 6.0 microns (C = 0 of the cyanoformamidyl group) which is consistent with the following structure:

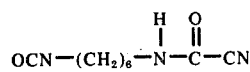

The nuclear magnetic resonance (NRM) spectrum was also consistent with the above structure.

The filtrate from the reaction product was kept dry, and the solvent was evaporated from the filtrate. The liquid residue weighed 104 grams. Since hexamethylene diisocyanate is soluble in petroleum ether and the corresponding cyanoformamidyl isocyanate is insoluble, the liquid residue was mixed with petroleum ether. Two liquid layers formed. The lower viscous layer was removed and again washed with petroleum ether. The petroleum ether extracts were combined and evaporated to leave a water white liquid which was mostly hexamethylene diisocyanate.

The viscous layer which was insoluble in petroleum ether was largely the desired hexamethylene cyanoformamidylisocyanate.

It is noted in the above example that pyridine is used as a catalyst. It has been found that the diisocyanates having an aliphatic organic moiety are less reactive than the diisocyanates having an aromatic organic moiety, and, accordingly, pyridine and other basic nitrogen containing compounds may be used when the diisocyanate has an aliphatic organic moiety.

EXAMPLE 3

A solution of 8.6 grams (0.32 mole) of hydrogen cyanide in 100 ml. of toluene is added to a solution of 72.3 grams (0.30 moles) of 4-(4'-isocyanatophenyl) cyclohexyl isocyanate in 200 ml. toluene at 5° C. Then 4 ml. of dibutyl tin diacetate is added and the temperature of the solution kept at 5°–10° C. for 4 hours. The solution is then allowed to slowly warm to room temperature. After several hours a solid separates from solution. The solid product is characterized by the following structure:

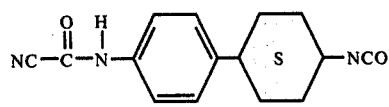

(Formed by addition of hydrogen cyanide to the more reactive aryl isocyanate group.)

EXAMPLE 4

To a cold (5° C.) solution of 51 grams (0.20 moles) of 4-(4'-isocyanatobenzyl) cyclohexyl isocyanate and 6.0 grams (0.22 moles) of hydrogen cyanide in 300 ml. of dry toluene is added 3 ml. of dibutyl tin di(isooctyl maleate). After stirring 3 hours, the solution is allowed to slowly warm to room temperature. During the next several hours a product characterized by the structure below slowly crystallizes from solution:

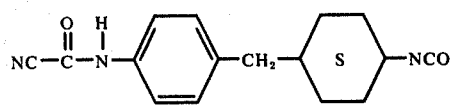

EXAMPLE 5

Five ml. of N,N-dimethylaniline is added to a solution of 60.6 grams (0.30 moles) of 3-(p-isocyanatophenyl)-propyl isocyanate and 8.1 grams (0.30 moles) of hydrogen cyanide in 250 ml. of dry toluene at 5° C. After several hours a product separates from solution characterized by the following structure:

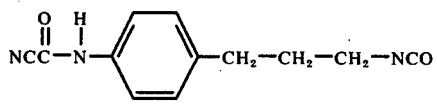

EXAMPLE 6

A solution of 6.5 grams (0.30 moles) of 3-(p-isocyanatophenyl)-1-methyl-propyl isocyanate and 8.1 grams (0.30 moles) of hydrogen cyanide in 200 ml. toluene is cooled to 5° C. Then 2 ml. of lutidine is added to the stirred solution which is kept at 5°-10° C. for 3 hours. The solution is then allowed to slowly warm to room temperature. After several hours a product separates characterized by the following structure:

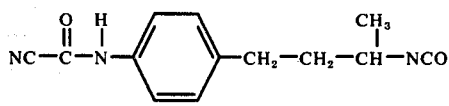

Here, again, the hydrogen cyanide adds much more easily to the less hindered and more reactive isocyanate group (aryl isocyanate instead of alkyl isocyanate).

EXAMPLE 7

One drop of triethylamine is added to a solution of 1 gram of methyl-1,3-phenylene cyanoformamidyl isocyanate (as made in Example 1) in 3 ml. of dimethylformamide at room temperature. Heat is liberated. After 3 minutes the product was diluted with toluene to precipitate a polymer which had an inherent viscosity of 0.10 in dimethylformamide (C, 0.5 grams/100 ml.) at 25° C. The infrared spectrum of the product exhibited absorption maximum at 3.05, 4.41 (very weak), 5.55, 5.74, and 5.98 microns.

EXAMPLE 8

To a solution of 6-cyanoformamidyl hexyl isocyanate in N-methyl pyrollidone is added triethylamine (1 ml.). The reaction solution became warm and very viscous within 10 minutes. After an hour the product was poured into toluene to precipitate a viscous gum. The organic solvents were decanted from the residue which was then stirred with additional toluene and this toluene again decanted from the product. The viscous gum was again stirred with toluene which was then evaporated in vacuo. The clear residue was polymeric. The infrared spectrum of the polymer had absorption maxima at 3.05, 5.55, 5.74, and 5.95 microns. A smear of the polymer on aluminum foil was heated on a hot plate at 100° F., and within 5 minutes the polymer formed a clear hard film which adhered strongly to the aluminum foil.

The cyanoformamidyl isocyanates of the present invention are useful as monomers in producing heterocyclic polymers. It is evident from the foregoing that this invention provides wholly new heterocyclic polymers which have, depending on their exact composition and molecular weights, widely varying properties which adapt them to a variety of uses. The polymers of the present invention may have from ten to one hundred or more repeating units, the repeating units consisting of two organic moieties and two imidazolidine rings. Heterocyclic polymers of the present invention are useful for making films, fibers, foams, molded objects, and the like. Films from the polymers of the present invention may be made by casting from solution or by forming under heat and pressure. The polymers are also useful in laminates and for making electrical insulators. The high temperature thermal stability of the polymers of the present invention allow them to be used in applications at elevated temperatures.

The polymers of the present invention are solids at room temperature. The soluble polymers melt over a range of temperatures, and some may have melting points greater than 250° C. Polymers of the present invention may be produced, which upon heating, may cross-link to insoluble and infusible polymers. Thus, the polymers may also be used as thermoset resins.

The nature and objects of the present invention having been completely described and illustrated, what I wish to claim as new and useful and secure by Letters Patent is:

1. Compositions of matter having the following formula:

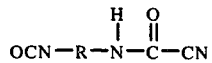

where:
R is an organic moiety which is aliphatic, alicyclic, aromatic, mixtures thereof and functionally substituted derivatives thereof, said derivatives being free of functional groups capable of reacting with hydrogen cyanide or isocyanate groups.

2. A composition of matter according to claim 1 wherein R is aliphatic.

3. A composition of matter according to claim 2 wherein R is hexamethylene.

4. A composition of matter according to claim 1 wherein R is aromatic.

5. A composition of matter according to claim 4 wherein R is methylphenylene.

6. A composition of matter according to claim 4 wherein R is 4, 4'-diphenylmethane.

7. A composition of matter according to claim 4, wherein R is 4, 4'-diphenyl ether.

8. A process for producing a cyanoformamidyl isocyanate which comprises: reacting 1 mole of hydrogen cyanide with 1 mole of a diisocyanate having the formula:

where
R is the organic moiety of the diisocyanate which may be aliphatic, alicyclic, aromatic, or mixtures thereof and functionally substituted derivatives thereof, said derivatives being free of functional groups capable of reacting with hydrogen cyanide or isocyanate groups, in a solvent at a temperature between −10° to 35° C in the presence of a suitable catalyst selected from the group consisting of dibutyl tin diacetate; dibutyl tin bis(isooctylmaleate); 2-picoline; quinoline; lutidine; N,N-dimethylaniline; N,N-diethylaniline and pyridine.

9. A process according to claim 8 wherein said diisocyanate is toluene diisocyanate and the catalyst is dibutyl tin diacetate.

10. A process according to claim 8 wherein said diisocyanate is hexamethylene diisocyanate and the catalyst is pyridine.

* * * * *